United States Patent [19]

van Oostveen et al.

[11] 4,027,678
[45] June 7, 1977

[54] PACING SYSTEM WITH CONNECTOR FOR CONNECTING ELECTRODE TO PACER

[75] Inventors: Arie A. van Oostveen, Laag-Keppel; Fred H. M. Wittkampf, Brummen, both of Netherlands

[73] Assignee: Vitatron Medical B.V., Dieren, Netherlands

[22] Filed: Nov. 19, 1975

[21] Appl. No.: 633,240

[52] U.S. Cl. .............................................. 128/419 P
[51] Int. Cl.² .......................................... A61N 1/36
[58] Field of Search ............... 128/404, 418, 419 P, 128/419 PT; 339/67, 69, 73, 94 R, 102 R, 113 R, 258 C, 271

[56] References Cited
UNITED STATES PATENTS

| 3,437,091 | 4/1969 | Jerushalmi et al. | 128/404 |
| 3,625,201 | 12/1971 | Murphy, Jr. | 128/419 PT |
| 3,649,367 | 3/1972 | Purdy | 128/419 P |
| 3,757,789 | 9/1973 | Shanker | 128/418 |
| 3,760,332 | 9/1973 | Berkovitz et al. | 128/418 |
| 3,871,382 | 3/1975 | Mann | 128/419 P |

OTHER PUBLICATIONS

Cordis' Omnicor Catalog 149-2340, Revo. 1974, pp. 1–15.

*Primary Examiner*—William E. Kamm
*Attorney, Agent, or Firm*—Woodcock Washburn Kurtz & Mackiewicz

[57] ABSTRACT

A connector device for use in connecting to a electrode pacing electrode, paticularly for connecting a pacer to an electrode where such pacer and electrode are from different manufacturers and are normally not adapted for connection one to another. The connector has a coil which is dimensioned to tightly receive a pronged end of the electrode, the receiving end being further formed in a mating way to receive the electrode so as to prevent current leakage at the situs of connection. The connector is adapted to permit connection or disconnection only as the connector is rotated in one given direction relative to the electrode. In one of the embodiments, the connector is housed in the pacer.

6 Claims, 5 Drawing Figures

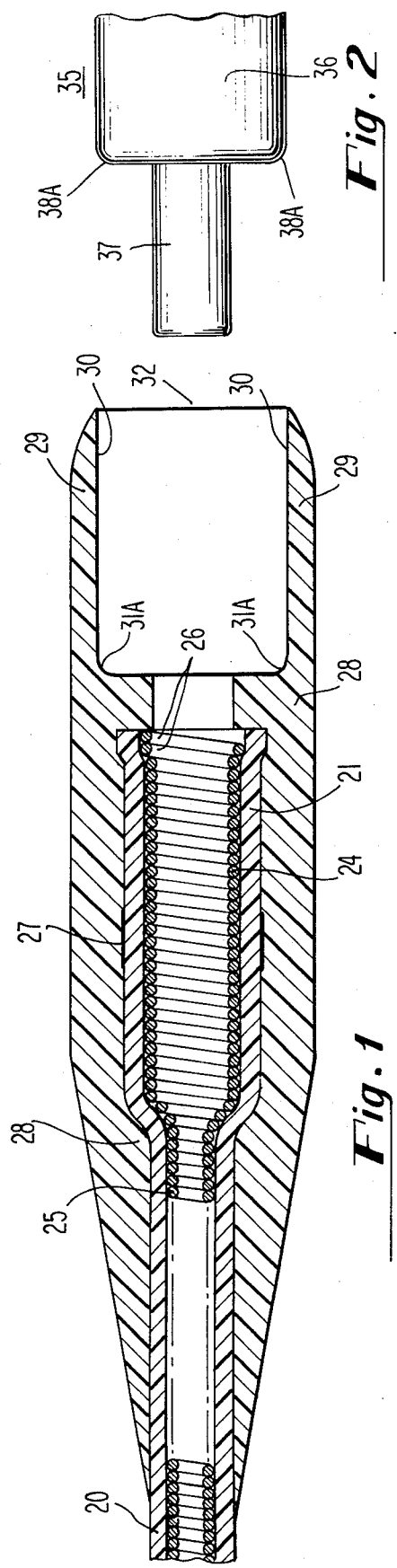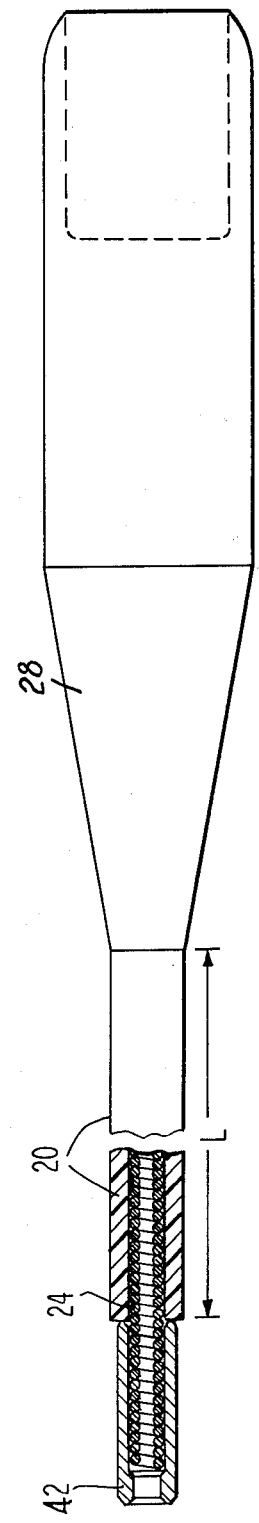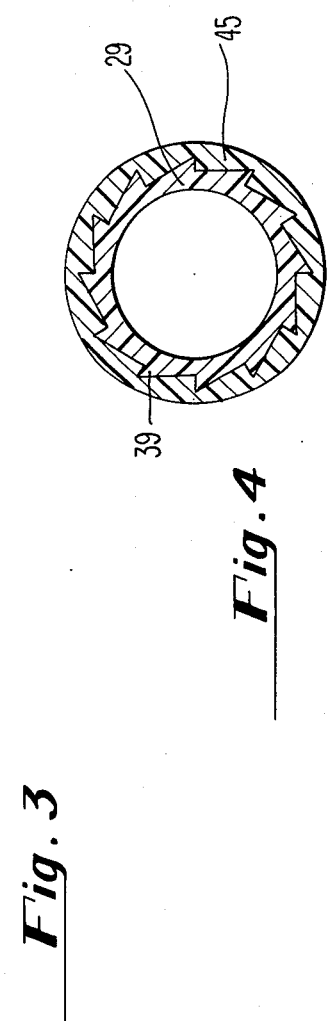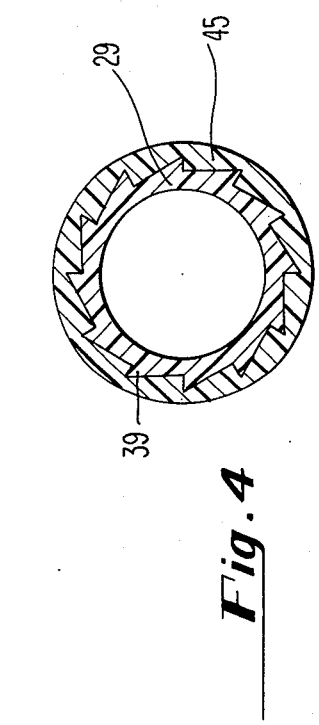

PACING SYSTEM WITH CONNECTOR FOR CONNECTING ELECTRODE TO PACER

BACKGROUND OF THE INVENTION

1. Field of the Invention

This invention lies in the area of connectors for cardiac pacing systems and, more particularly, connectors for connecting electrodes and electronic pacers which are normally not compatible for connection.

2. Description of the Prior Art

Cardiac pacing systems, wherein the heart is stimulated by signals generated by electronic devices known as Pacemakers, or pacers, have become widely used since the inception of the pacer industry in about the early 1960's. Basically, a pacer system normally requires two components, namely the pacer itself to generate the signals, and an electrode which has one end connected to the output of the pacer and the other end positioned within the patient's heart, the electrode serving the function of delivering the generated stimulus signals from the pacer to the heart. The electrode, sometimes referred to as a catheter, also delivers sensed natural cardiac signals back to the pacer in systems that operate on a demand basis. The methods of insertion of the electrode through a portion of the patient's cardiovascular system and of positioning the distal stimulating tip thereof at the proper place in the heart, are well known and documented.

With the increased use of cardiac pacing systems, there have been a number of manufacturers which have produced either pacers or electrodes or both. As a result of the relatively quick proliferation of such manufacturers over the last decade, there have appeared a variety of electrode and pacer designs, without any uniformity or standardization of the means of connecting one to the other. As can be expected, any given manufacturer who produces both devices designs them to be connectable, but as a rule an electrode of a first manufacturer will not normally connect to a pacer of a second company, and vice versa. This causes a substantial problem to the physician who sets out to implant a pacer of one manufacturer and has only the electrode of another, or who wishes to replace, in a patient who has an ingrown electrode of a first make, an old pacer with a new pacer of a different make.

As a result of the above difficulties, there are now commercially available connectors, or adapters, to enable connection of unmatched pacer-electrode pairs. However, such connectors are generally not satisfactory, for a variety of reasons. Some require screwing of the electrode to the connector; some require the application of insulating adhesive paste; and some even require cutting of the electrode to adapt it to the connector, which is even less desirable. What is needed, and indeed has been an acutely felt need in this area, is a connector which can be manipulated easily and reliably by the physician, and without the need of any unwanted ancillary operations.

SUMMARY OF THE INVENTION

It is an objective of this invention to provide a quick and reliable connector for connecting an electrode to a pacer.

It is another objective of this invention to provide a connector for electrical connection to a pacing electrode, the connection being reliably strong for long term inplantation.

It is another objective of this invention to provide means adapted for connecting an electrode to a pacer without the need for auxiliary materials or tools. It is another objective of this invention to provide a pacing system with the connector being housed in the pacer.

It is another objective of this invention to provide a quick and reliable connector for connection to an electrode so that there is no current leakage at the connection.

It is another objective of this invention to provide a connector which may be connected to an implanted electrode to effectively lengthen the electrode.

It is a still further objective of this invention to provide a connector which may be incorporated into a pacer, for reliable connection of an electrode directly to the pacer.

In accordance with the above objectives, there is provided a connector adapted for receiving and tightly holding the end of an electrode, having an axial opening with a coil positioned therein and dimensioned to receive the conductor prong of the electrode in a good electrical contact and with a friction fit, and an outer opening positioned relative to the coil to snugly engage the end of the electrode casing so that there is no leakage from the outside into the area of electrical contact. The other end of the conductor is fitted for insertion into the pacer.

BRIEF DESCRIPTION OF THE DRAWINGS

FIG. 1 is a cross sectional view of the distal end of one embodiment of the connector of this invention.

FIG. 2 is a diagrammatic view of the proximal end of an electrode to which the connector of FIG. 1 can be connected.

FIG. 3 is a cross sectional view of the connector of this invention, showing connection to a pacer terminal.

FIG. 4 is an end cross sectional view of another embodiment of the connector of this invention, showing means for permitting only one way rotation of the connector.

DESCRIPTION OF THE PREFERRED EMBODIMENTS

Figure 5:
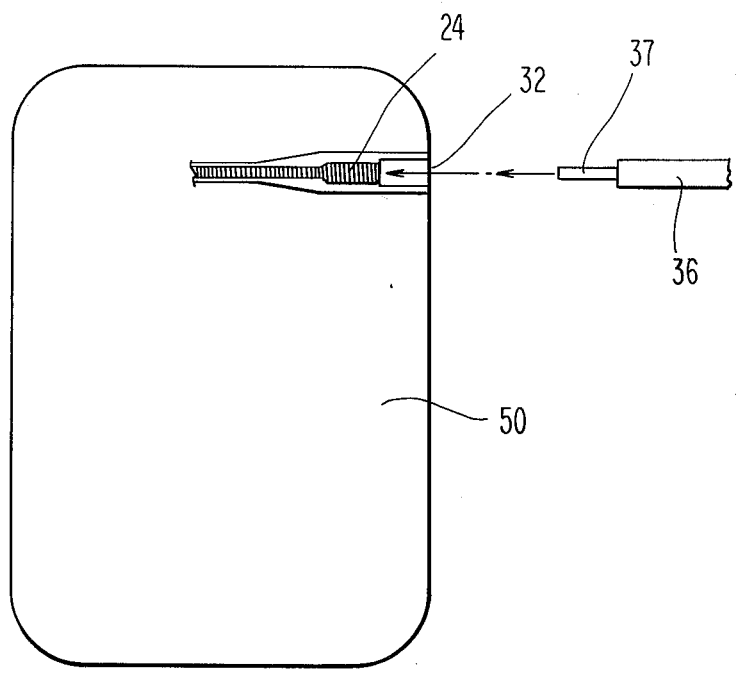
FIG. 5 is a schematic representation of an embodiment wherein the connector of this invention is housed in a pacer.

Referring now to FIG. 1, there is shown the distal end of the connector, being the end which is connected to the electrode. A casing 20, suitably made of silicone rubber, covers a helical coil 24, which coil is made of a material such as elgiloy which is a good conductor. The conductor 24 need not be a coil for the portion 25 thereof which is displaced away from the end opening, but it is preferably hollow so that a mandrin, or stylet, can be passed through the connector and the electrode. The portion of the conductor 24 which is adjacent the distal end is a coil, and is wound so that it can be displaced under tension very slightly radially outwardly. The portion of casing 20 which surrounds the distal coil portion 24 is identified by the numeral 21. The end portion 26 of coil 24 may suitably have several turns of slightly greater diameter, to permit or guide entry of a blunt electrode prong such as prong 37 shown in FIG. 2. Over top of, or around the outside of the end of casing 20, there is placed a silicone rubber outer casing 28, having an end portion 29 which contains an opening 32 defined by inner wall 30. The geometry of wall 30 is shaped to mate, or register with the geometry of the proximal end of the casing 36 of the electrode 35, as shown in FIG. 2. Note that the contour of corners 31A of the connector matches those of 38A on the electrode. The mated opening 32 permits a snug fitting of the electrode tip into the connector. At the other, or proximal end, of the connector, the coil 24 is extended beyond the casing 20 to provide a suitable connecting prong for connection to the pacer terminal 42.

In practice, there will be different geometries, or configurations of the proximal end of the electrode 36, and so the opening 32 may be contoured accordingly. The invention embraces any form of opening 32, the opening being limited only in being matched to the electrode which is to be connected. Likewise, the proximal terminal of the connector may have different configurations, for connection to different pacers. The length L of the connector is, for most applications, not important, but may be made to be any desired length for applications where it is desired to effectively lengthen an implanted electrode.

In operation, the opening 32 is placed over the prong 37 of the electrode, and the connector is moved axially toward the electrode until prong 37 enters coil 24. At this point, the physician turns the connector in a given manner, either clockwise or counter-clockwise according to the direction of winding 24. Prong 37 enters coil 24 only if the connector is rotated in the proper direction. This is because for rotation in one direction the end of coil 24 will be pushed out, causing radial expansion of the coil which permits entry of the electrode; while for rotation in the other direction the end of the coil is pinched inward, blocking entry. The inside diameter of coil 24 is made to be just smaller than the outer diameter of prong 37, so that there is a friction fit which provides both an excellent mechanical and electrical connection.

In order to release the electrode from the connector, the connector must be turned in the same angular direction, since the same forces relative to the coil operate whether connecting or disconnecting. In order to indicate the proper direction of rotation, there is imprinted an arrow 27, or other suitable indicia, on the outside of casing 20 and relatively near the distal end. Since the outer casing 28 is substantially transparent, the arrow can be seen, and yet will not be worn off due to handling.

A further means of ensuring proper rotation is illustrated in FIG. 4. Casing 28 is provided with protruding notch portions 39, and around casing 28 is positioned rotatable element 45 which has complimentary notch portions arranged in ratchet-like fashion so as to inhibit rotation in the improper direction and allow it only in the proper direction. Element 45 may also suitably be made of silicone rubber or any material of like or equivalent characteristics. As illustrated in the drawing, there is little clearance between element 45 and casing 29, but element 45 can be rotated clockwise because the notches 39 are sufficiently flexible.

It is to be noted that while the invention has been described as being particularly applicable to a cardiac pacing system, it may be used as well for making connections in other types of bioelectric or physiological detection and control systems. The invention as claimed in terms of a cardiac pacing system embraces equally other equivalent systems.

The invention may further comprise a pacer 50 for generating stimulus signals, with the connector being housed in the pacer 50, as illustrated in FIG. 5.

We claim:

1. A connector adapted for connecting a pacer to an electrode, where said electrode has a proximal end with a conductor prong of predetermined diameter and a casing of predetermined geometry, said connector being adapted at its distal end to connect to said proximal electrode end and at its proximal end to a pacer terminal, said connector comprising:
   a. an inner coil extending through the length of said connector, said coil having at a distal portion an inside diameter just smaller than said conductor prong predetermined diameter, said coil further having several end turns of slightly larger diameter at said distal end, whereby entry of said electrode prong into said coil is facilitated;
   b. an inner casing surrounding said coil, said casing extending substantially the length of said connector;
   c. an outer casing around said inner casing at said connector distal end, said outer casing having a portion extending axially distal of the end of said coil, said extending portion having an opening with geometry substantially matching said predetermined electrode casing geometry;
   d. proximal end means at the proximal end of said connector for providing mechanical and electrical connection of said coil to a pacer terminal; and
   e. means for allowing rotation of said connector relative to said electrode in only one direction.

2. The connector as described in claim 1, wherein said inner casing has imprinted on the outside thereof rotation indicia, and said outer casing is substantially transparent.

3. A connector adapted for connecting a pacer to an electrode, where said electrode has a proximal end with a conductor prong of predetermined diameter and a casing of predetermined geometry, said connector being adapted at a first end to connect to said electrode proximal end and at its other end to a pacer terminal, comprising:
   a. conducting means for providing an electrical conduction path from said first connector end to said other connector end;
   b. mating means located at said first connector end for mating with said electrode proximal end; and
   c. said conducting means having an end portion at said first end adapted for electrical and mechanical engagement and disengagement of said conductor prong therewith only as said connector is rotated in direction relative to said electrode.

4. The connector as described in claim 3, wherein said conducting means comprises an inner axially hollow conductor, and said conductor has an inside diameter at its distal end just smaller than said conductor prong diameter and several turns at the distal end thereof of slightly larger diameter than the other turns.

5. The connector as described in claim 4, wherein said connector is of a predetermined length, whereby when connected to said electrode it effectively adds said length to said electrode.

6. The connector as described in claim 3, and further in combination with a pacer for generating stimulus signals, said connector other end being housed in said pacer and said conducting means being connected at said connector other end to the output of said pacer.

* * * * *

UNITED STATES PATENT AND TRADEMARK OFFICE
CERTIFICATE OF CORRECTION

PATENT NO. : 4,027,678
DATED : June 7, 1977
INVENTOR(S) : Arie A. van Oostveen and Fred H. M. Wittkampf It is certified that error appears in the above-identified patent and that said Letters Patent are hereby corrected as shown below:

In the Abstract, line 1, delete "electrode".

Column 4, line 52, before "direction", insert --the same--.

Signed and Sealed this sixteenth Day of August 1977

[SEAL]

Attest:

RUTH C. MASON
*Attesting Officer*

C. MARSHALL DANN
*Commissioner of Patents and Trademarks*